United States Patent
Pirkle et al.

(10) Patent No.: US 10,234,404 B2
(45) Date of Patent: Mar. 19, 2019

(54) LIQUID SCANNING SYSTEM AND METHOD FOR IV DRUG VERIFICATION AND IDENTIFICATION

(71) Applicant: Battelle Memorial Institute, Columbus, OH (US)

(72) Inventors: Wesley C. Pirkle, New Albany, OH (US); Richard L. Shoaf, Westerville, OH (US); Raphael J. Welsh, Powell, OH (US)

(73) Assignee: Battelle Memorial Institute, Columbus, OH (US)

( * ) Notice: Subject to any disclaimer, the term of this patent is extended or adjusted under 35 U.S.C. 154(b) by 149 days.

(21) Appl. No.: 15/128,027

(22) PCT Filed: Oct. 17, 2014

(86) PCT No.: PCT/US2014/061252
§ 371 (c)(1),
(2) Date: Sep. 21, 2016

(87) PCT Pub. No.: WO2015/142384
PCT Pub. Date: Sep. 24, 2015

(65) Prior Publication Data
US 2017/0097307 A1    Apr. 6, 2017

Related U.S. Application Data

(60) Provisional application No. 61/969,041, filed on Mar. 21, 2014.

(51) Int. Cl.
| G01N 22/00 | (2006.01) |
| G01N 29/024 | (2006.01) |
| G01N 29/032 | (2006.01) |
| G01N 29/28 | (2006.01) |
| G01N 29/32 | (2006.01) |
| G01N 29/44 | (2006.01) |
| A61J 1/10 | (2006.01) |
| G01N 33/15 | (2006.01) |
| G06K 7/10 | (2006.01) |
| G06K 7/14 | (2006.01) |

(52) U.S. Cl.
CPC ............... *G01N 22/00* (2013.01); *A61J 1/10* (2013.01); *G01N 29/024* (2013.01); *G01N 29/032* (2013.01); *G01N 29/28* (2013.01); *G01N 29/326* (2013.01); *G01N 29/4436* (2013.01); *G01N 33/15* (2013.01); *G06K 7/10366* (2013.01); *G06K 7/1413* (2013.01); *A61J 2205/10* (2013.01); *A61J 2205/30* (2013.01); *A61J 2205/60* (2013.01); *G01N 2291/011* (2013.01); *G01N 2291/015* (2013.01); *G01N 2291/022* (2013.01)

(58) Field of Classification Search
CPC .................................................... G01N 22/00
See application file for complete search history.

(56) References Cited

U.S. PATENT DOCUMENTS

2010/0026300 A1*  2/2010  Klein ..................... G01N 22/00
                                                            324/316

* cited by examiner

*Primary Examiner* — Manuel A Rivera Vargas
(74) *Attorney, Agent, or Firm* — Benesch, Friedlander, Coplan & Aronoff LLP

(57) ABSTRACT

A system and method are disclosed for interrogating a liquid in a container. The liquid sample, such as drugs in a liquid base, is identified based on a radio frequency and/or ultrasonic measurement.

26 Claims, 10 Drawing Sheets

LIQUID SCANNING SYSTEM AND METHOD FOR IV DRUG VERIFICATION AND IDENTIFICATION

CROSS-REFERENCE TO RELATED APPLICATIONS

This application is a U.S. national stage entry under 35 U.S.C. § 371(c) of International Pat. App. No. PCT/US14/61252, which claims priority from U.S. Provisional Patent Application No. 61/969,041, filed on Mar. 21, 2014, each of which is entirely incorporated by reference herein.

BACKGROUND

Systems and methods for screening and identifying liquid filled containers are known in the art and include systems and methods for detecting and distinguishing hazardous materials. For example, U.S. Provisional Application No. 61/892,138, filed on Oct. 17, 2013, now U.S. application Ser. No. 14/517,686 filed on Oct. 17, 2014, and assigned to Battelle Memorial Institute, which is incorporated by reference herein in its entirety, discloses a container screening system and method for detecting and distinguishing hazardous materials at airports using both radio frequency (RF) and ultrasonic (US) systems.

The ever increasing use of automation and technology in manufacturing requires use of automated quality control and assurance systems to prevent manufacturing defects and human error. Chemical and pharmaceutical manufacturing account for a large portion of worldwide manufacturing. The present application appreciates that identification of chemical and pharmaceutical solutions and compositions may be a challenging endeavor.

SUMMARY

In one embodiment, a method of interrogating a liquid sample is provided, the method of interrogating a liquid comprising the steps of: placing a container with a liquid sample in a test fixture; providing an input radio frequency (RF) signal at a frequency between 100 MHz and 15 GHz; introducing the input RF signal to the container with the liquid sample by at least one of: one or more transmitting wide band antennas, one or more transmitting narrow band antennas, a coaxial probe providing the input RF signal, a conductive pattern providing the input RF signal, and a grid array providing the input RF signal; receiving at least one of: a reflected RF signal, and a coupled RF signal, the at least one received signal generated from the introduction of the input RF signal to the container with the liquid sample, and the reflected RF signal received from at least one of: one or more receiving wide band antennas, one or more receiving narrow band antennas, a coaxial probe providing the at least one received signal, a conductive pattern providing the at least one received signal, and a grid array providing the at least one received signal; analyzing at least one of the input RF signal and the at least one received signal in at least one of a frequency domain or time domain for a measurement of at least one of: one or more S-parameters, a Q factor, a center frequency, a level of impedance match, a current, a voltage drop, a time domain measurement, a frequency domain measurement, a Fast Fourier Transform (FFT) ratio of two or more measurements, an FFT difference of two or more measurements, a measurement to which a time domain algorithm has been applied, measurements to which a Partial Least Squares (PLS) regression has been applied, wherein the measurement of at least one of the input RF signal and the at least one received signal is one of a real value, an imaginary value, a magnitude, and a phase; comparing the measurement of at least one of the input RF signal and the at least one received signal against one or more baseline measurements in a database; and identifying a liquid or predicting an identity of a liquid from the compared measurements.

In another embodiment, a method of interrogating a liquid sample is provided, the method of interrogating a liquid comprising the steps of: placing a container with a liquid sample in a test fixture; coupling an ultrasonic (US) transducer to the container with the liquid sample in the test fixture with at least one couplant; generating a high-voltage pulse in an US pulse generator; sending the high-voltage pulse from the US pulse generator to the US transducer; generating an US wave in the US transducer from the high-voltage pulse; propagating the US wave through the couplant to the container with the liquid sample to produce one or more pulse echoes to be received by the US transducer; employing a delay between the propagated US wave and the one or more produced pulse echoes; receiving the one or more produced pulse echoes at the US transducer to produce an analog signal; transmitting the analog signal to an analog to digital converter (ADC) to digitize the transmitted analog signal; analyzing the digitized signal to determine an US velocity of the liquid sample; comparing the US velocity of the liquid sample against one or more baseline US velocities in a database; and identifying a liquid or predicting an identity of a liquid from the compared US velocities.

In another embodiment, a method of interrogating a liquid sample is provided, the method of interrogating the liquid sample comprising the steps of: placing a container with a liquid sample in a test fixture; coupling at least one of an ultrasonic (US) transmitter to one side of the container with the liquid sample in the test fixture with at least one couplant, and coupling an US receiver to another side of the container with the liquid sample in the text fixture with at least one couplant; generating and transmitting an US signal from the US transmitter through the container with the liquid sample; employing a delay after the US signal is transmitted and before the transmitted US signal is received; receiving the transmitted US signal as an analog signal at the US receiver on the another side of the container with the liquid sample; transmitting the analog signal to an analog to digital converter (ADC) to digitize the transmitted analog signal; analyzing the digitized signal to determine an US velocity of the liquid sample; comparing the US velocity of the liquid sample against one or more baseline US velocities in a database; and identifying or predicting an identity of a liquid from the compared US velocities.

In another embodiment, a method of interrogating a liquid sample is provided, the method of interrogating a liquid comprising the steps of: placing a container with a liquid sample in a test fixture; coupling an ultrasonic (US) transducer to the container with the liquid sample in the test fixture with at least one couplant; generating a high-voltage pulse in an US pulse generator; sending the high-voltage pulse from the US pulse generator to the US transducer; generating an US wave in the US transducer from the high-voltage pulse; propagating the US wave through the couplant to the container with the liquid sample to produce one or more pulse echoes to be received by the US transducer; employing a delay between the propagated US wave and the one or more produced pulse echoes; receiving the one or more produced pulse echoes at the US transducer to produce an analog signal; transmitting the analog signal to an analog to digital converter (ADC) to digitize the transmitted analog signal; analyzing the digitized signal to determine an attenuation of the one or more pulse echoes caused by the liquid sample; comparing the attenuation of the one or more pulse echoes against one or more baseline attenuations in a database; and identifying a liquid or predicting an identity of a liquid from the compared attenuations.

In another embodiment, a method for verifying a drug/solution mixture contained in an intravenous (IV) bag is provided, the method for verifying a drug/solution mixture contained in an IV bag comprising the steps of: receiving a liquid-filled IV bag for test; determining a presence of at least one of a barcode, machine-readable object, radio frequency identification (RFID) tag, and text identifying a liquid in the liquid-filled IV bag; scanning the at least one present barcode, machine-readable object, RFID tag, and text to generate an input data; comparing the input data with baseline data in a database to determine if the input data exists in the database; alerting a system user if the input data does not exist in the database; placing the liquid-filled IV bag in a test fixture; applying a predetermined amount of pressure to the liquid-filled IV bag in the test fixture; transmitting a radio frequency (RF) signal to interrogate the liquid-filled IV bag in the test fixture; receiving the transmitted RF signal after the transmitted RF signal interrogates the liquid-filled IV bag in the test fixture; coupling an ultrasonic (US) device to the liquid-filled IV bag in the test fixture to complete an US measurement; taking a path length distance measurement; measuring a temperature of the liquid-filled IV bag in the test fixture; applying a temperature compensation based on the measured temperature to all baseline RF signals and US measurements in a database; analyzing the received RF signal and US measurement against all baseline RF signals and US measurements in the database; identifying a drug/solution mixture or predicting an identity of a drug/solution mixture based on the analysis of the received RF signal and US measurement against all baseline RF signals and US measurements in the database; and providing an operator the identification of the drug/solution mixture, and printing or affixing at least one of a barcode, a machine-readable object, and RFID tag, and a text to the liquid-filled IV bag to indicate a content of the liquid-filled IV bag.

BRIEF DESCRIPTION OF THE DRAWINGS

The accompanying figures, which are incorporated in and constitute a part of the specification, illustrate various example systems and methods, and are used merely to illustrate various example embodiments.

DETAILED DESCRIPTION

Figure 1:
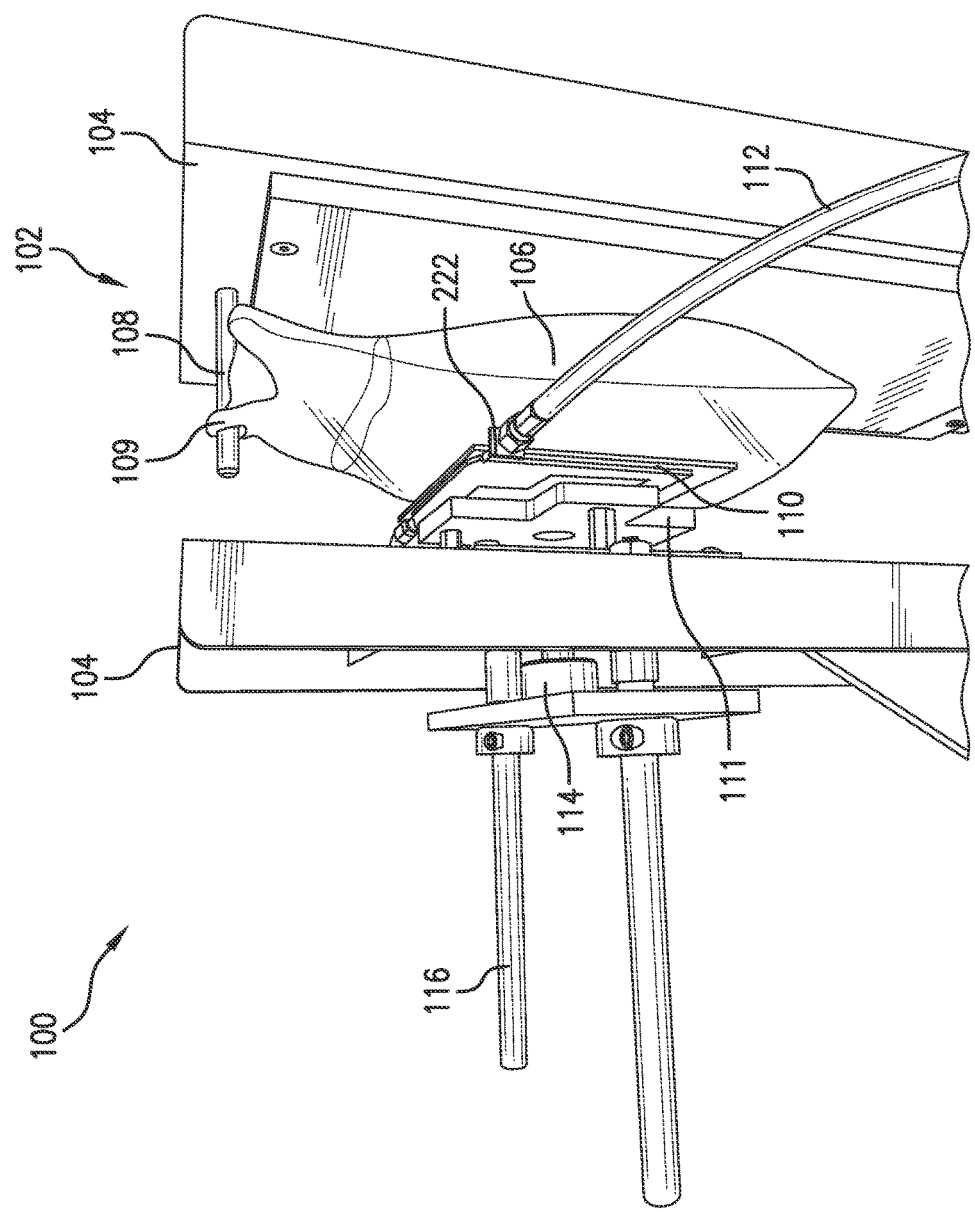
FIG. 1 illustrates a perspective view of an example embodiment of a liquid scanning system for IV drug verification and identification.

FIG. 1 illustrates a perspective view of an example embodiment of a liquid scanning system 100 for IV drug verification and identification. Liquid scanning system 100 may be used to accurately identify and verify pharmaceuticals and liquid solutions that have been placed in IV bags, syringes, and other containers used for holding liquid drug mixtures. Liquid scanning system 100 may include a test fixture 102 for conducting liquid scanning in a controlled, repeatable test environment. Test fixture 102 may include one or more vertical plates 104, between which a container with liquid sample 106 may be placed. One or more vertical plates 104 may have a container mounting hardware 108 thereon for affixing container with liquid sample 106. Container with liquid sample 106 may have a standardized feature 109 thereon to interface with container mounting hardware 108. In one embodiment, standardized feature 109 is an IV bag loop operable for use with a standardized IV bag stand or IV bag pole. Standardized feature 109 interfacing with container mounting hardware 108 may ensure consistent placement of container with liquid sample in test fixture 102. Test fixture 102 may also include mount 111 for attaching RF sensor 110 thereon. Mount 111 may provide a sturdy attachment point for RF sensor 110 to ensure that RF sensor 110 is repeatedly mounted in a same position in test fixture 102. RF sensor 110 may include an input and output jack 222 for attaching a wire 112. Wire 112 may be used to transmit an RF signal to input jack 222 for use with sensor 110 for interrogating container with liquid sample 106. In one embodiment, in place of RF sensor 110, a narrow-band or wide-band antenna (not shown) may be used for interrogating container with liquid sample 106. Wire 112 may also be used to transmit an output RF signal from output jack 222 to be analyzed by a processor or computing device (not shown). In one embodiment, wire 112 is a coaxial cable. An output RF signal may include a reflected RF signal or a coupled RF signal. RF sensor 110 may include one or more input and output jacks 222. In one embodiment, RF sensor may have one jack 222 designated as input jack 222 and may have one jack 222 designated as output jack 222. In another embodiment, jack 222 may be both input jack 222 and output jack 222. Input/output jack 222 may be a connection for connecting coaxial type cables. In a non-limiting example, input/output jack 222 may be a male/female BNC connector to interface with a corresponding connector on wire 112. In another non-limiting example, input/output jack 222 are one of: F-type connectors, N-type connectors, RF connectors, and UHF connectors which connector to a corresponding connection on wire 112 to secure wire 112 to input/output jack 222. Behind RF Sensor 110 and mount 111 may be a pressure sensor 114 to measure how much pressure is being exerted on container with liquid sample 106 by vertical plates 104. Pressure sensor 114 may interface with one or more control devices (not shown) to automatically adjust the pressure exerted by vertical plates 104 on container with liquid sample 106. In one embodiment, pressure sensor 114 on detecting a certain pressure may output a detected pressure to a control device or processor (not shown) to control an electric motor (not shown) to automatically move vertical plate 104 back and forth along cylinder slide 116 relative to detected pressure from pressure sensor 114.

Figure 2:
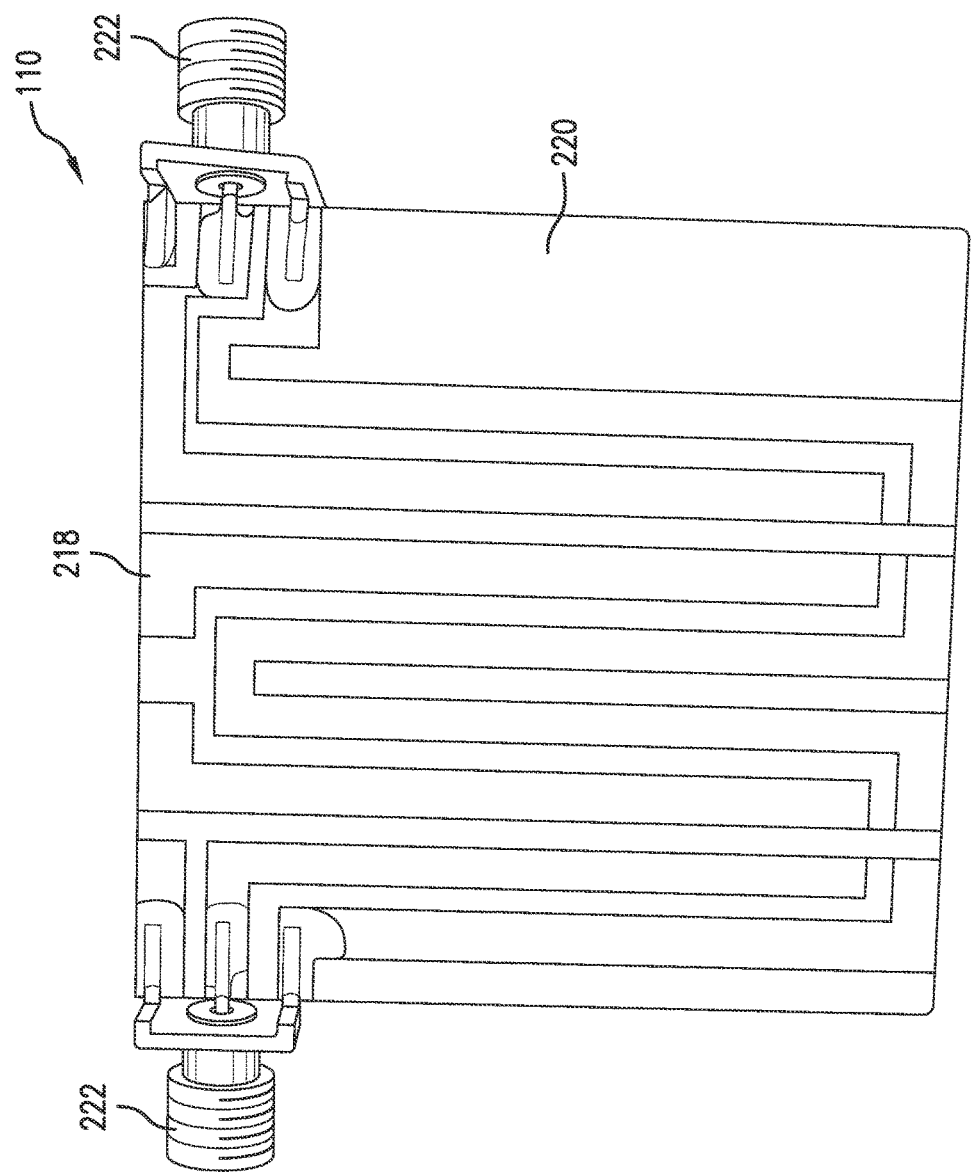
FIG. 2 illustrates a perspective view of an example RF sensor.

Referring to FIG. 2, perspective view of an example RF sensor 110 is illustrated. RF sensor 110 may be used to sense an output RF signal such as a reflected output signal or a coupled output signal. Output RF signal may result from a transmitted RF input signal reflecting off of container with liquid sample 106 and being received by RF sensor 110 to be output as an output RF signal. Output RF signal may result from a direct coupled input signal interacting with container with liquid sample 106 to provide a coupled output RF signal to RF sensor 110. RF sensor may include a conductive trace 218 on non-conducting substrate 220. Conductive trace 218 may be used to conduct and carry both an input and output RF signal to input and output jacks 222. In one embodiment, conductive trace 218 touches container with liquid sample 106 to produce a coupled RF output signal carried on conductive trace 218 to output jack 222. Output jack 222 may further convey coupled RF output signal to wire 112 such that RF signal can be further transmitted to a processor or computer for further signal processing and analysis. In one embodiment, sensor 110 is used in addition to transmitted RF signals from one or more antennas (not shown) to interrogate container with liquid sample 106. In this embodiment, compared to antennas, sensor 110 will not emit much, if any, RF energy. Antennas for transmitting and receiving RF signals may include wide band antennas and narrow band antennas.

Figure 3:
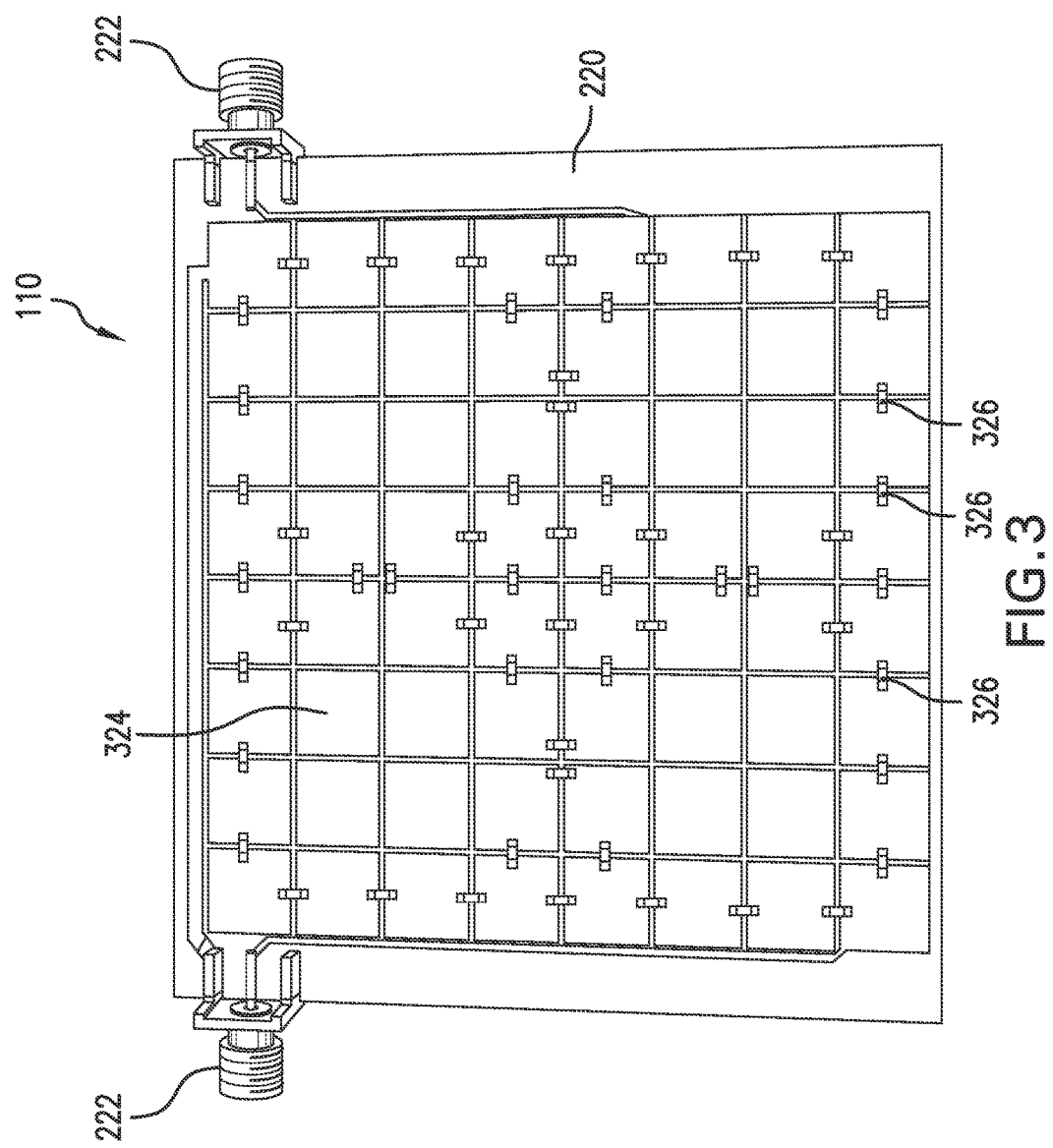
FIG. 3 illustrates a perspective view of an example RF sensor.
Figure 4:
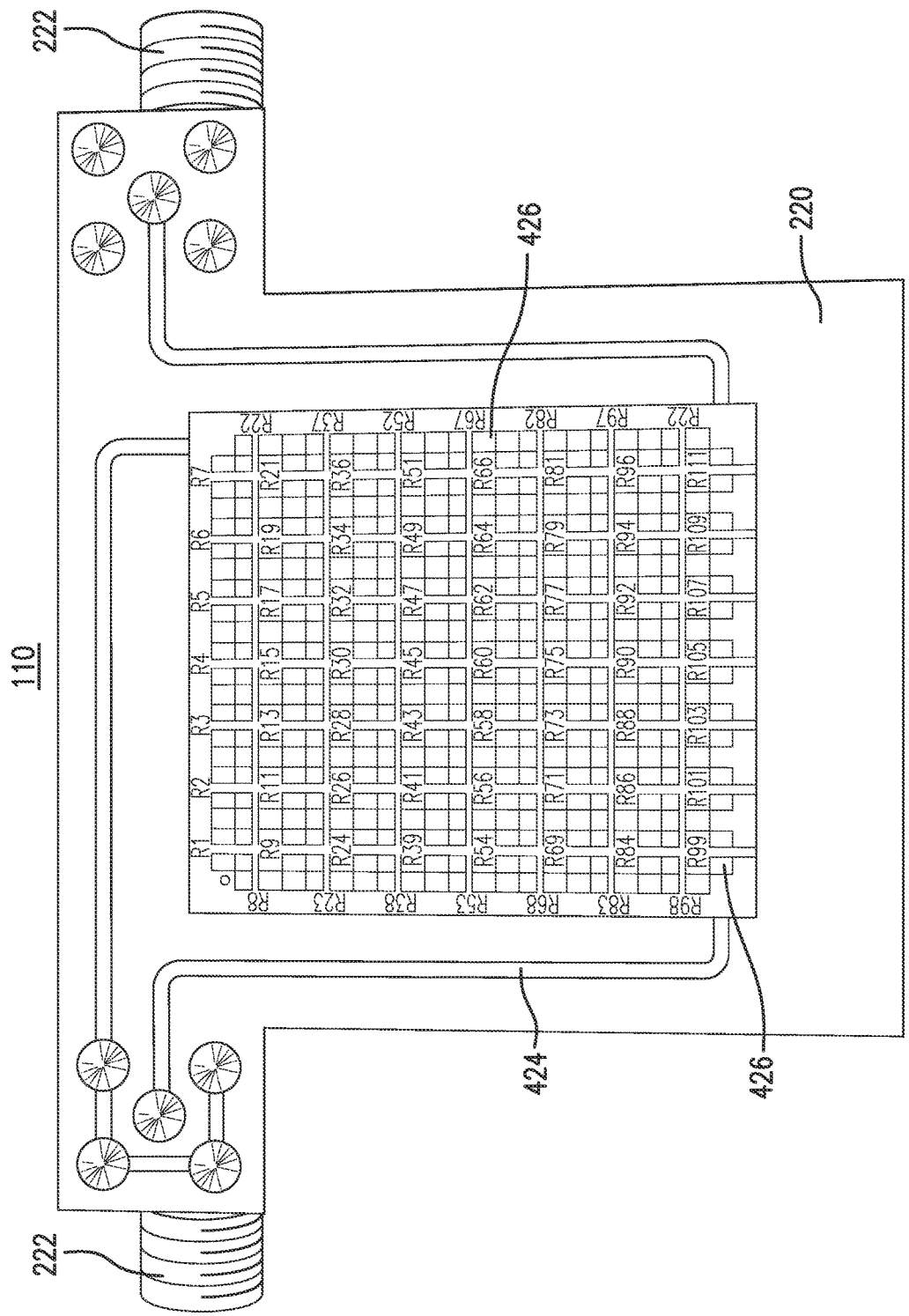
FIG. 4 illustrates a perspective view of an example RF sensor.

Referring to FIGS. 3 and 4, perspective views of other example RF sensors 110 are illustrated respectively. RF sensor 110 may be used to sense an output RF signal such as a reflected output signal or a coupled output signal. Output RF signal may result from a transmitted RF input signal reflecting off of container with liquid sample 106 and being received by RF sensor 110 to be output as an output RF signal. Output RF signal may result from a direct coupled input signal interacting with container with liquid sample 106 to provide a coupled output RF signal to RF sensor 110. With reference to FIG. 3, RF sensor 110 may be a grid array of diodes 326 arranged on a matrix of conductive portions 324. Conductive portions 324 may be separated by non-conducting substrate 220 and some of conductive portions 324 may be interconnected by diodes 326. Since diodes 326 only allow current to pass in one direction, RF signal will be routed through sensor 110 in a particular pattern or direction. Diodes in diode array of RF sensor 110 may be arranged based on required operating parameters of RF sensor 110. Similarly, with reference to FIG. 4, RF sensor may be a grid array of resistive elements 426 arranged on a matrix of conductive portions 424. Conductive portions 424 may be separated by non-conducting substrate 420 and some of conductive portions 424 may be interconnected by resistive elements 426. In one embodiment, resistive elements 426 are resistors. RF sensor 110 may include one or more input and output jacks 222. Again, a same input jack 222 may also be used as an output jack 222 for inputting and outputting an RF signal.

RF signals output by output jack 222 may be further conveyed via wire 112 to a processor or computer (not shown) for further signal processing. Both input and output RF signals may be further analyzed and processed by a computer, processor, and other like systems. RF signals may be analyzed in both a time and frequency domain. In one embodiment, a fast Fourier transform (FFT), discrete Fourier transform (DFT), or like algorithm may be used to convert an RF signal in a time domain to an RF signal in a frequency domain and vice-versa. RF signals may be analyzed by a computer or signal processor such as a digital signal processor (DSP) or spectrum analyzer. Input or output signal may be analyzed for a measurement of at least one or more S-parameters, a Q factor, a center frequency, a level of impedance match, a current, and a voltage drop. Measurements may also include a time domain measurement, a frequency domain measurement, a Fast Fourier Transform (FFT) ratio of two or more measurements, an FFT difference of two or more measurements, a measurement to which a time domain algorithm has been applied, and measurements to which a Partial Least Squares (PLS) regression has been applied. Measurements may be a real value, an imaginary value, a complex value, a magnitude, or a phase. In one embodiment, signals and measurements are processed and analyzed with computer hardware and software designed for such analysis, processing, computation, and comparison of such signals and measurements. In one embodiment, a computer running MATLAB® software is used to process and analyze signals, parameters and measurements. In another embodiment, a computer operatively connected to a memory or computer readable medium with baseline measurements thereon, is used to compare analyzed and processed signals, parameters, characteristic, and measurements against signals of known reference and baseline samples to provide an output which identifies, or reasonably predicts, an identity of a liquid sample based on similar characteristics, parameters, and measurements of known reference and baseline samples.

Liquid scanning system 100 may include either a temperature probe (not shown) or standoff probe (not shown) for determining a temperature of a container with liquid sample undergoing interrogation. Temperature measurements may be used to determine a temperature compensation factor which may be applied to known reference and baseline samples stored in a database. In one embodiment, liquid scanning system 100 may automatically apply a temperature compensation factor to known reference and baseline samples based on a temperature of container with liquid sample 106. In one embodiment, standoff probe for determining a temperature of a container with liquid sample undergoing interrogation is an infrared (IR) sensor.

Figure 5:
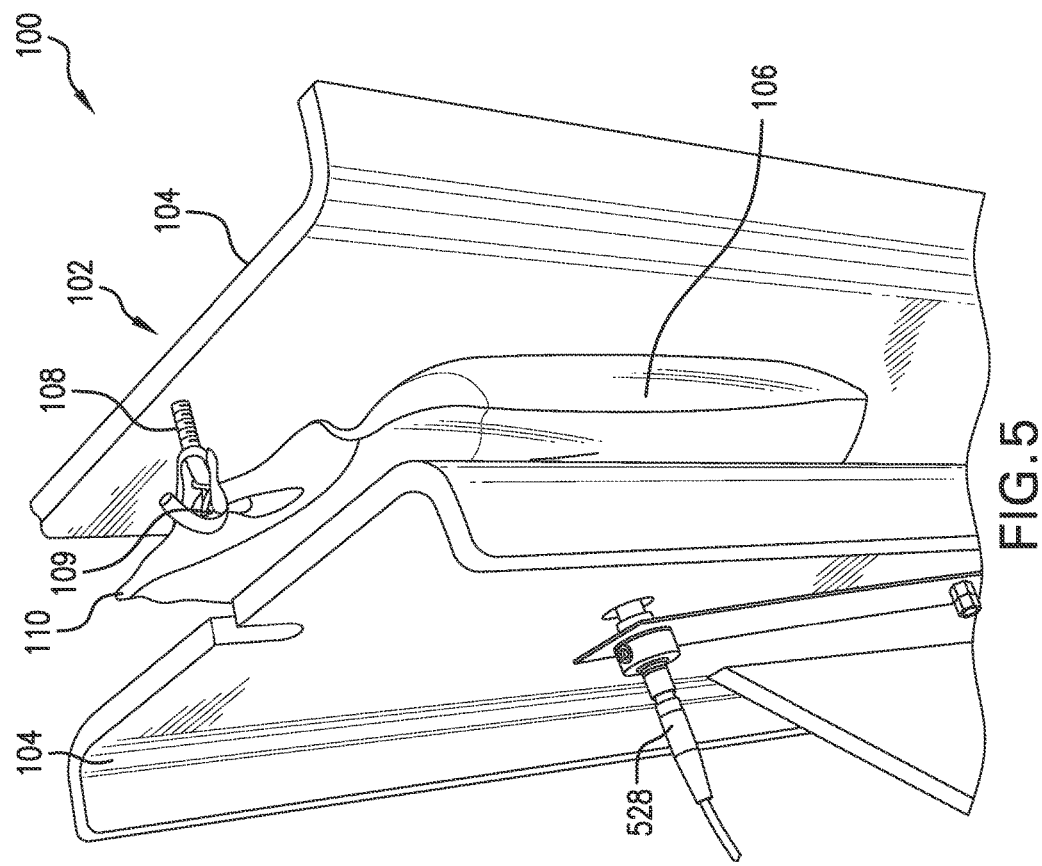
FIG. 5 illustrates a perspective view of an example embodiment of a liquid scanning system for IV drug verification and identification.

Referring to FIG. 5, a perspective view of an example embodiment of a liquid scanning system 100 for IV drug verification and identification is illustrated. In place of RF sensor 110 to provide an RF signal to container with liquid sample 106, FIG. 5 illustrates an example embodiment using an ultrasonic (US) device 528. US device 528 may be one of an US pulse generator that generates a high voltage signal for use by an US transducer, an US transducer for generating and receiving a pulse signal and echo pulse; an US transmitter for transmitting an US signal through container with liquid sample 106, or an US receiver for receiving a transmitted signal through a container with liquid sample 106. US device 528 may be coupled to container with liquid sample by one of a dry or liquid couplant (not shown) for better propagation of an US signal or pulse through container with liquid sample 106. US device 528 may also include one of an analog to digital converter (ADC) (not shown) for converting a received analog echo pulse or transmitted US signal to provide a better signal for analysis and processing.

US device 528 may also use a delay line or delay circuit (not shown) to provide for better signal accumulation. Because of a velocity at which an US signal or pulse propagates through a medium and sample such as container with liquid sample 106, a delay line may be used to delay data collection from US transducer 528 and US receiver 528 to prevent unnecessary data collection. Test device 102 may also use pressure sensor 104 with US receiver 528 to provide a same pressure to container with liquid sample 106 for each test.

Figure 6:
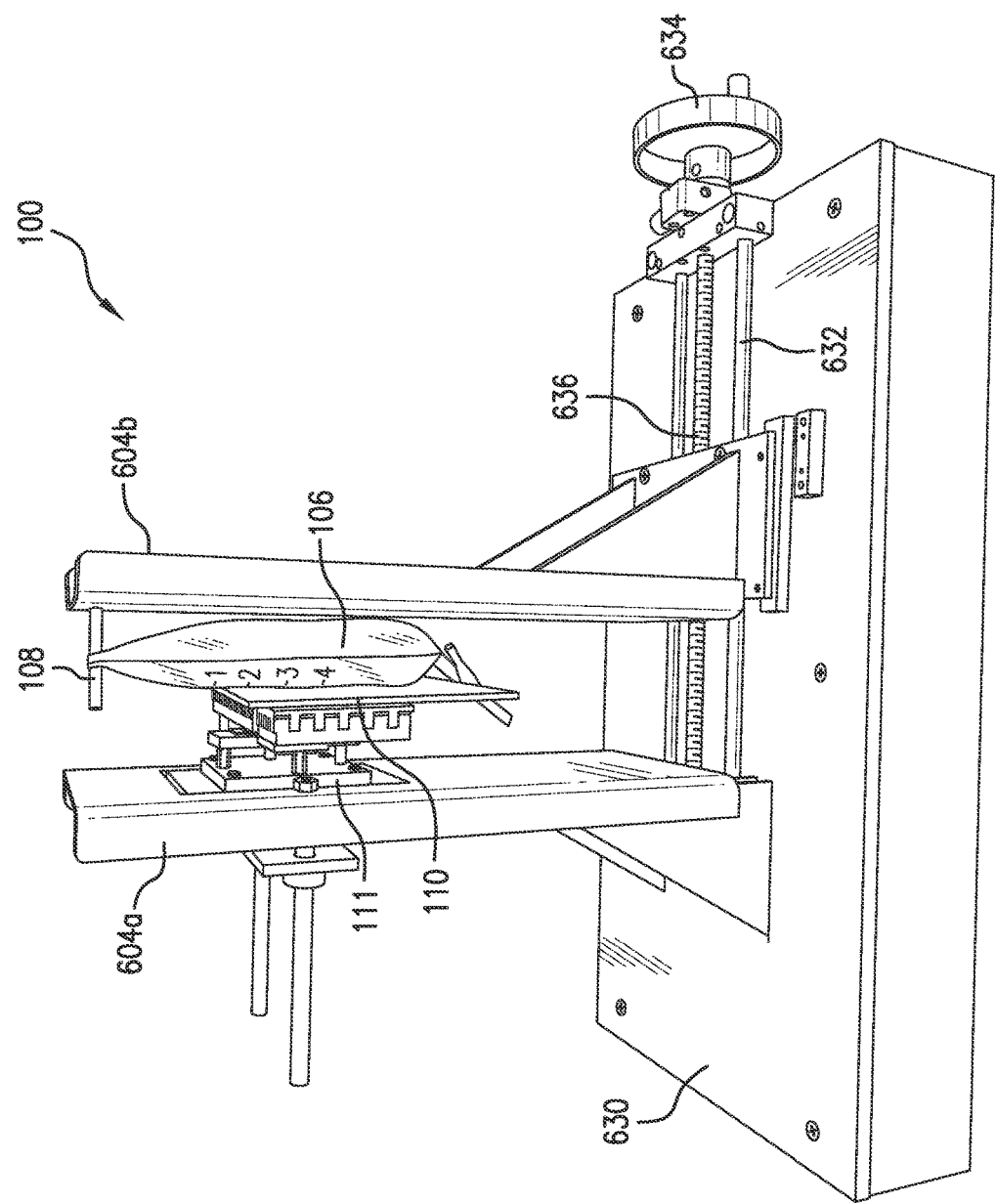
FIG. 6 illustrates a perspective view of an example embodiment of a liquid scanning system for IV drug verification and identification.

Referring to FIG. 6, a perspective view of an example embodiment of a liquid scanning system 100 for IV drug verification and identification is illustrated. Liquid scanning system 100 may include a test platform 630 upon which vertical plates 604a, 604b are operably connected. In one embodiment, one vertical plate 604a is immovably mounted to test platform 630 while another movable vertical plate 604b moves linearly toward and away from fixed, immovable vertical plate 604a. Movable vertical plate 604b may include hardware to affix movable vertical plate 604b to slider rails 632. Crank mechanism 634 may be operatively connected to linear driver 636, and linear driver 636 may be operatively connected to movable vertical plate 604b. Rotation of crank mechanism 634 may drive linear driver 636 to actuate movable vertical plate 604b towards and away from fixed vertical plate 604a depending on a direction of rotation of crank mechanism 634. For example, rotating crank mechanism 634 in a clockwise direction may move movable vertical plate 604b toward fixed vertical plate 604a. In one embodiment, linear driver 636 is a threaded rod. In another embodiment, linear driver 636 may be a linear actuator. Crank mechanism 634 may be replaced with an electric motor and various sensors may be employed to further automate and control movement of movable vertical plate 604b towards and away from fixed vertical plate 604a. Indicia (not shown) may be provided on test platform 630 to give a general length/distance measurements between fixed platform 604a and movable platform 604b, between RF sensor 110 and movable platform 604b, as well as providing an indication of a thickness of container with liquid sample 106. Measuring path length—that is, a thickness of container with liquid sample 106, may provide a path length distance measurement which may a necessary value for calculating an ultrasonic velocity. In one embodiment, a sensor (not shown) for sensing path length feeds sensed path length back into a control system to compensate/adjust for a desired path length and/or a desired pressure sensed by pressure sensor 114.

While liquid scanning system 100 for IV drug verification and identification has been illustrated with example test setups in a laboratory environment, test setups illustrated are non-limiting examples used to illustrate a utility of liquid scanning system 100. It is understood that liquid scanning system 100 may be packaged in a more commercially practical package. Such a commercial package may include all of the functionality of liquid scanning system 100 for IV drug verification and identification as described herein. In addition, a commercially packaged liquid scanning system 100 may be automated and further poka-yoked to assist an operator using liquid scanning system 100. For example, a commercial embodiment of systems described herein, may require an operator to insert an IV bag, syringe, or other container in a certain orientation (i.e. upright, lying flat, with a longitudinal axis orthogonal to RF sensor 110, etc.) before liquid scanning system 100 may be used to ensure a consistency of measurements.

Figure 7:
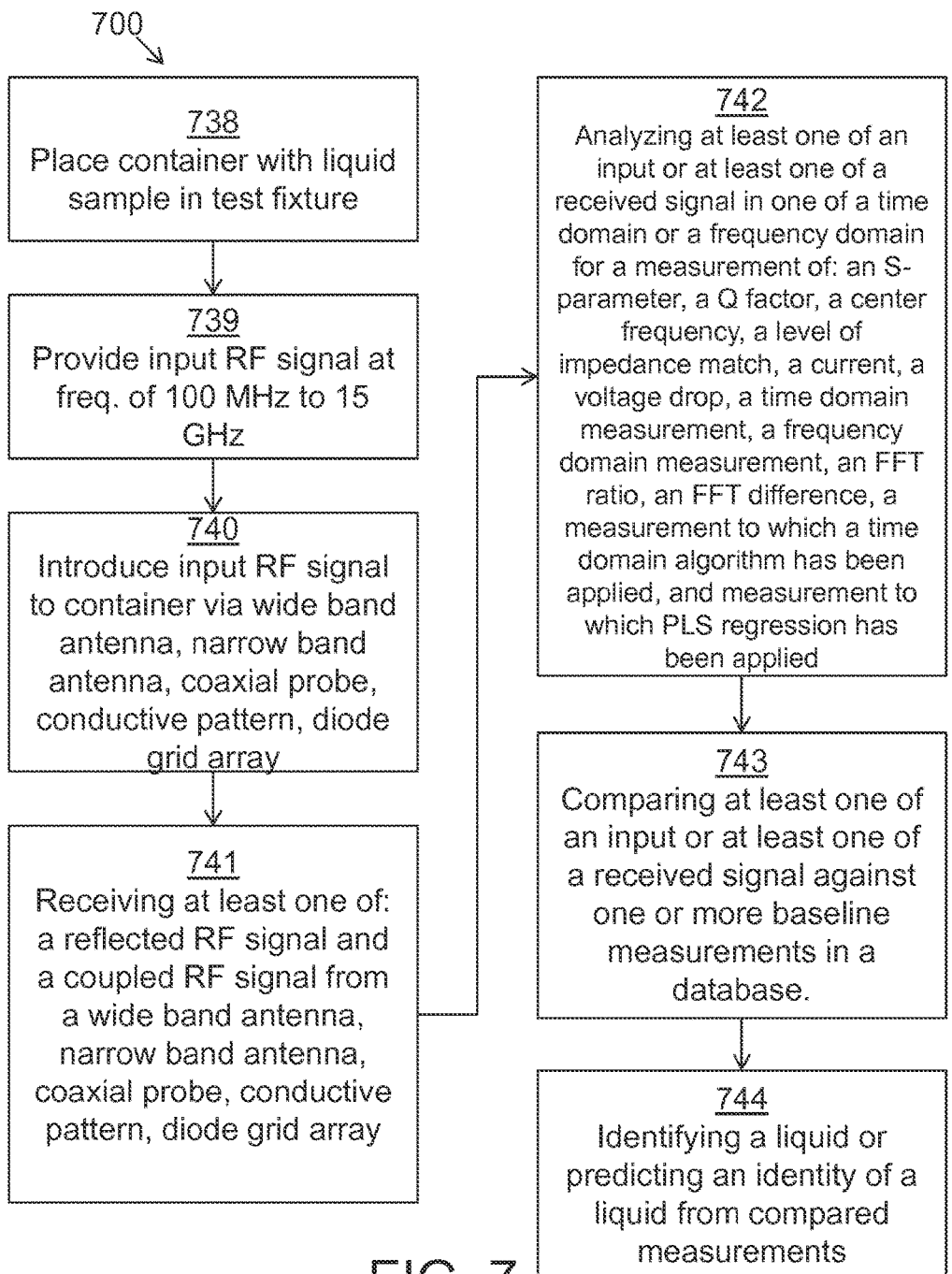
FIG. 7 illustrates a flow chart of an example method for using a liquid scanning system for IV drug verification and identification.

FIG. 7 is a flow chart of one embodiment of a method 700 for interrogating a liquid sample using an RF signal. In one embodiment, method 700 includes placing a container with a liquid sample in a test fixture (738). Method 700 also may include providing an input RF signal at a frequency between 100 MHz and 15 GHz (739). In one embodiment, input RF signal at a frequency between 100 MHz and 15 GHz is an RF signal with a fixed frequency between 100 MHz and 15 GHz. In another embodiment, input RF signal at a frequency between 100 MHz and 15 GHz is a frequency sweep with a varying frequency between 100 MHz and 15 GHz. Frequency sweep with a varying frequency between 100 MHz and 15 GHz may change frequency continuously from a set minimum frequency to a set maximum frequency or from a set maximum frequency to a set minimum frequency. In one embodiment, set minimum frequency is 100 MHz. In another embodiment, set maximum frequency is 15 GHz. Set minimum and maximum frequencies may be user defined. Frequency sweep may be at a defined rate, for example, 5 MHz/sec, 20 MHz/sec, 100 MHz/sec, and the like. Method 700 may also include introducing an RF signal to a container with a liquid sample by at least one of: one or more transmitting wide band antennas; one or more transmitting narrow band antennas; a coaxial probe providing an input RF signal; a conductive pattern (trace) providing an input RF signal; and a diode grid array providing an input RF signal (740). In one embodiment, antennas, coaxial probes, a conductive trace RF sensor, and a grid array RF sensor are all used in RF signal interrogation of a liquid sample. Method 700 may also include receiving at least one of a reflected RF signal and a coupled RF signal, at least one received signal generated from an introduction of an input RF signal to a container with a liquid sample, and received from at least one of: one or more receiving wide band antennas, one or more receiving narrow band antennas, a coaxial probe providing at least one of a reflected RF signal and a coupled RF signal; a conductive pattern providing at least one of a reflected RF signal and a coupled RF signal; and a grid array providing at least one of a reflected RF signal and a couple RF signal (741). Method 700 may also include analyzing at least one of an input RF signal and at least one of a received signal in at least one of a frequency domain or a time domain for a measurement of at least one of: an S-parameter (i.e. $S_{11}$, $S_{12}$, $S_{21}$, $S_{22}$), a Q factor, a center frequency, a level of impedance match, a current, and a voltage drop, wherein a measurement of at least one of an input RF signal and at least one of a received signal is one of a real value, an imaginary value, a complex value, a magnitude, and a phase (742). Method 700 may also include comparing at least one of an input or at least one of a received signal against one or more baseline measurements in a database (743). Method 700 may also include identifying a liquid or predicting an identity of a liquid from compared measurements (744). Measurements may also include time domain and/or frequency domain measurements to which a Fast Fourier Transform (FFT) algorithm may be applied. An FFT may be applied to input RF signal measurements, received signal measurements, and other baseline measurements to provide transform values. Ratios and differences of FFT transform values may also be used to identify a liquid, and develop a liquid signature which may be stored in a database. Further time domain based algorithms may be applied to measurements to identify unknown liquids. Partial Least Squares (PLS) regression analysis of measurements, FFT transform value ratios. FFT transform value differences, and measurements to which time domain based algorithms have been applied may be used to generate regression values, and regression values may be used to identify a liquid.

In addition to using an RF signal to interrogate a liquid, method 700 may also include use of US interrogation to interrogate a liquid.

Figure 8:
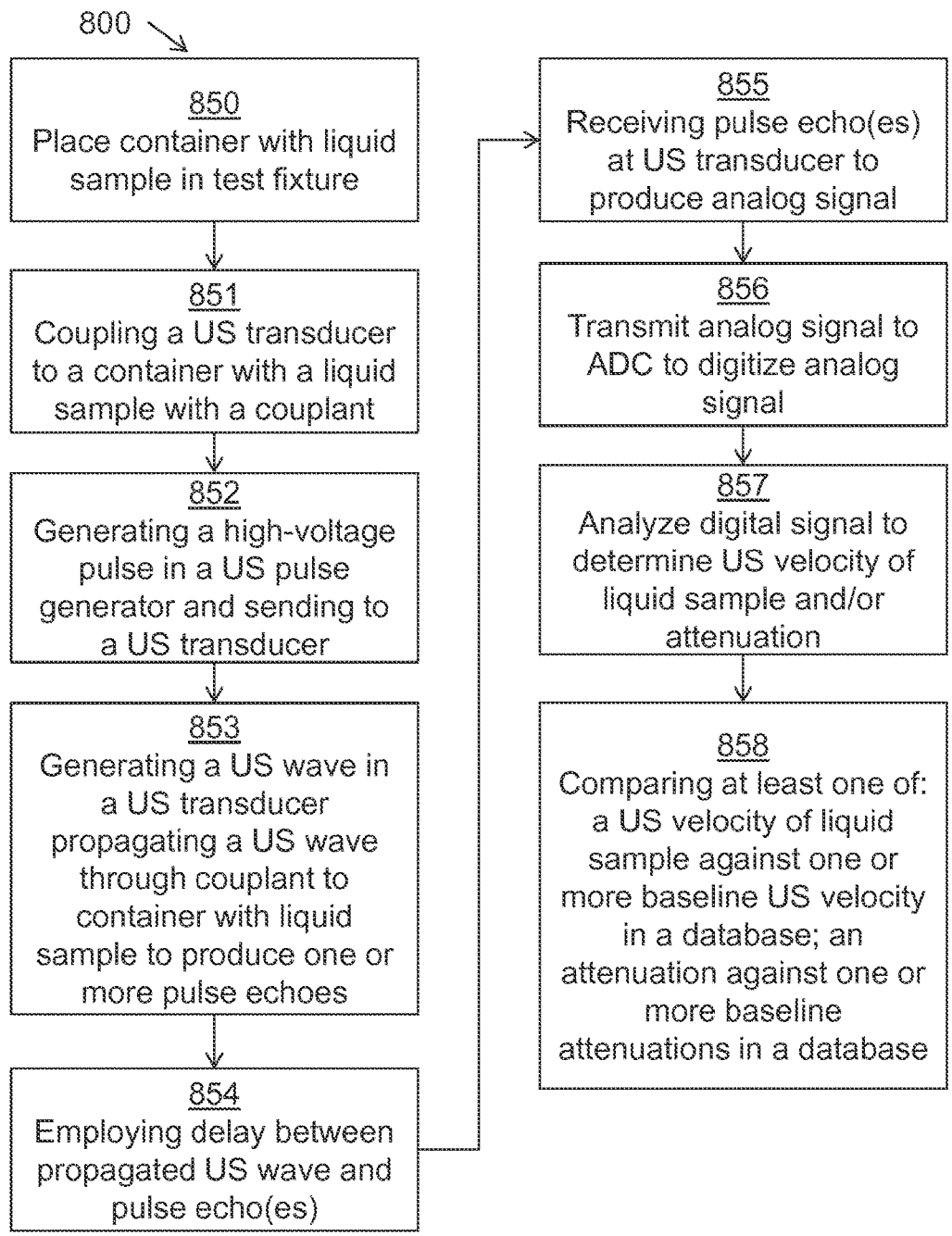
FIG. 8 illustrates a flow chart of an example method for using a liquid scanning system for IV drug verification and identification.

FIG. 8 is a flow chart of one embodiment of a method 800 for interrogating a liquid sample using an US pulse echo. Method 800 may include placing a container with a liquid sample in a test fixture (850). US transducer may be coupled to a container with a liquid sample in a test fixture with at least one of a liquid and solid couplant (851). A high-voltage pulse may be generated in a US pulse generator and sent from a US pulse generator to a US transducer (852). An US wave may be generated in a US transducer from a high-voltage pulse and propagated through a couplant to a container with a liquid sample to produce one or more pulse echoes to be received by an US transducer (853). A delay may be employed between a propagated US wave and one or more produced pulse echoes (854). One or more produced pulse echoes may be received at a US transducer to produce an analog signal (855). An analog signal may be transmitted to an analog to digital converter (ADC) to digitize a transmitted analog signal (856). A digitized signal may be analyzed to determine an US velocity of a liquid sample and/or attenuation of the one or more pulse echoes caused by the liquid sample (857). An US velocity of a liquid sample and/or an attenuation of the one or more pulse echoes caused by the liquid sample may be compared against one or more baseline US velocities and/or attenuations in a database, respectively, and a liquid may be identified or an identity of a liquid may be predicted from compared US velocities and/or attenuations (858).

In addition to using a US pulse echo, method 800 may also include at least one of RF signal interrogation and US signal interrogation.

Figure 9:
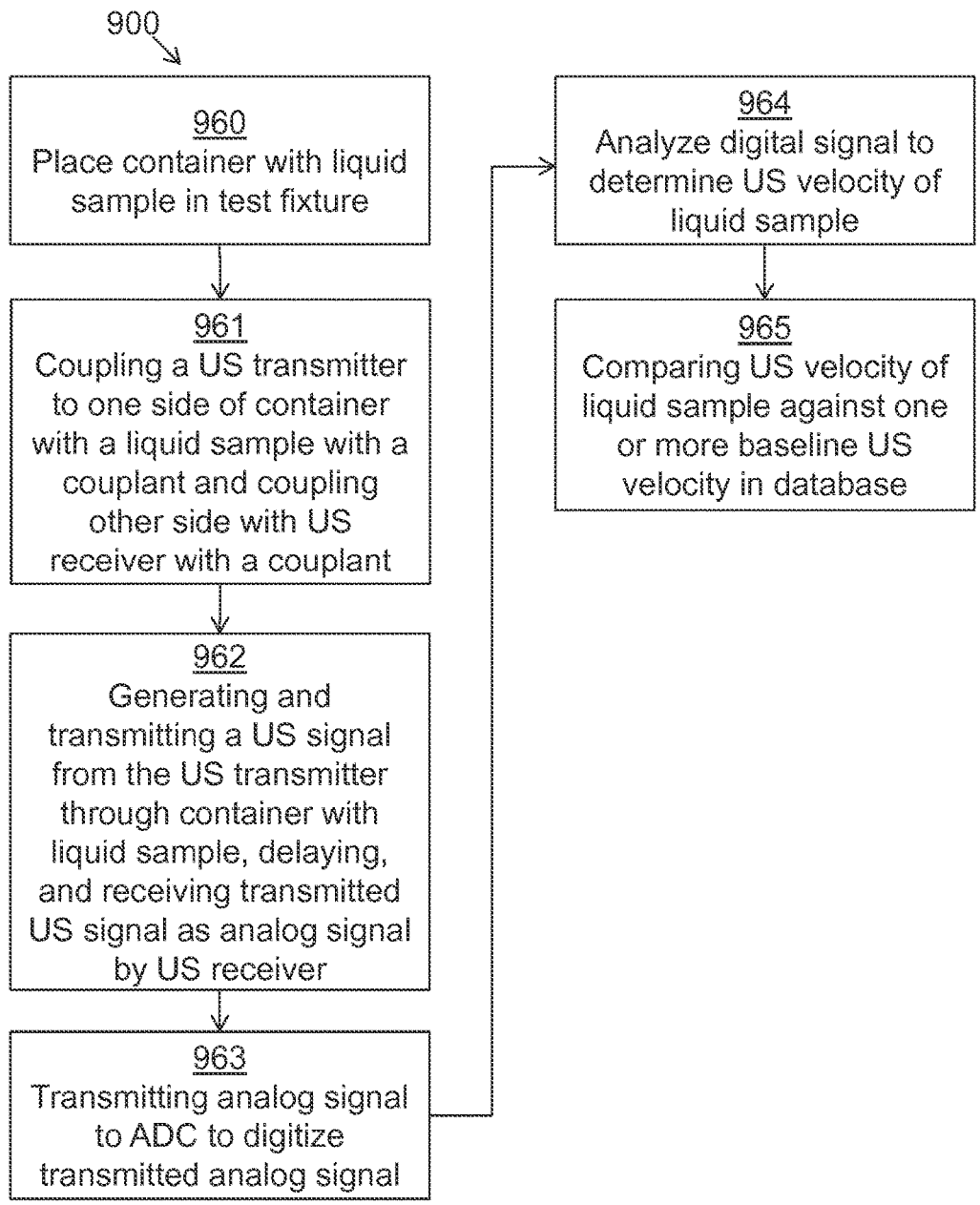
FIG. 9 illustrates a flow chart of an example method for using a liquid scanning system for IV drug verification and identification.

FIG. 9 is a flow chart of one embodiment of a method 900 for interrogating a liquid sample using an US signal. In one embodiment, method 900 may include placing a container with a liquid sample in a test fixture (960). At least one US transmitter with at least one couplant may be coupled to one side of a container with a liquid sample and an US receiver with at least one couplant may be coupled to another side of a container with a liquid sample (961). An US signal may be generated and transmitted from an US transmitter through a container with a liquid sample, and a delay may be employed after an US signal is transmitted, and before a transmitted US signal is received, and a transmitted US signal may be received as an analog signal at an US receiver on another side of a container with a liquid sample (962). An analog signal may be transmitted to an analog to digital converter (ADC) to digitize a transmitted analog signal (963). A digitized signal may be analyzed to determine an ultrasonic velocity of the liquid sample (964). An US velocity of a liquid sample may be compared against one or more baseline ultrasonic velocities in a database, and a liquid may be identified from ultrasonic velocities of known liquid signatures stored in the database, or an identity of an unknown liquid may be predicted based on compared ultrasonic velocities (965).

In addition to using US signal interrogation to identify a liquid, method 900 may include at least one of RF signal interrogation and US pulse echo interrogation.

Figure 10:
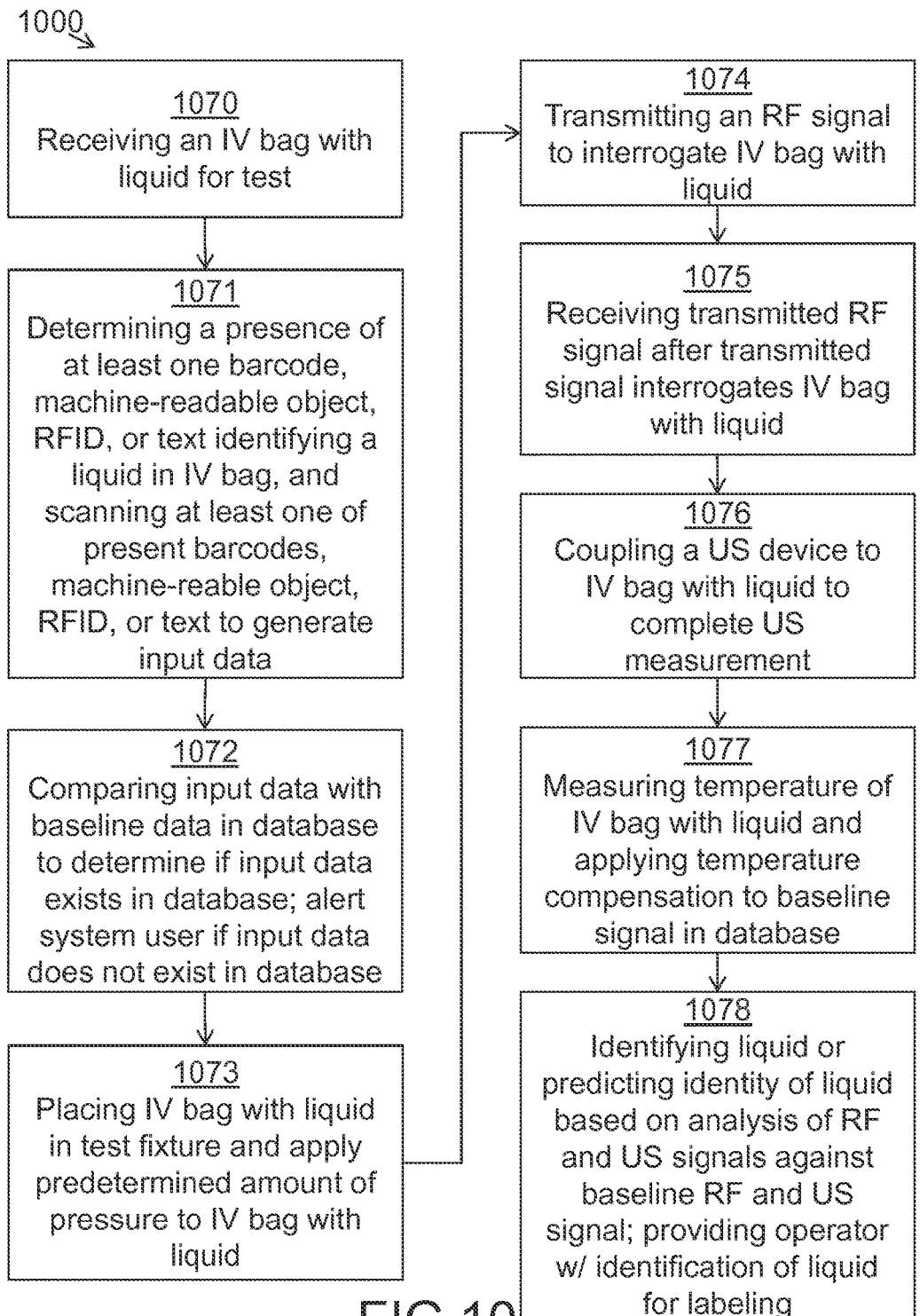
FIG. 10 illustrates a flow chart of an example method for using a liquid scanning system for IV drug verification and identification.

FIG. 10 is a flow chart of one embodiment of a method 1000 for verifying a drug and solution mixture contained in an intravenous (IV) bag. In one embodiment, method 1000 may include receiving a liquid-filled IV bag (1070). In one embodiment, method 1000 may also include determining a presence of at least one of a barcode, a machine-readable object, a radio frequency identification (RFID) tag, and text to identify a liquid in a liquid-filled IV bag, and scanning at least one present barcode, machine-readable object. RFID tag, and text to generate an input data (1071). In an absence of determining a presence of at least one of a barcode, a machine-readable object, a RFID tag, and a text in (1071), method 1000 may skip to step (1073). In one embodiment, method 1000 may also include comparing an input data with a baseline data in a database to determine if an input data exists in a database and alerting a user if an input data does not exists in a database (1072). In one embodiment, method 1000 may also include placing a liquid-filled IV bag in a test fixture and applying a predetermined amount of pressure to a liquid-filled IV bag in a test fixture (1073). In one embodiment, method 1000 may also include transmitting a RF signal to interrogate a liquid-filled IV bag in a test fixture (1074). In one embodiment, method 1000 may also include receiving a transmitted RF signal after a transmitted signal interrogates a liquid-filled IV bag in a test fixture (1075). In one embodiment, method 1000 may also include coupling an US device to a liquid-filled IV bag in a test fixture to complete an US measurement (1076). In one embodiment, method 1000 may also include measuring a temperature of a liquid-filled IV bag in a test fixture and applying a temperature compensation based on a measured temperature to all baseline RF signals and US measurements in a database (1077). In one embodiment, method 1000 may also include identifying a drug/solution mixture or predicting an identity of a drug/solution mixture based on an analysis of a received RF signal and US measurement against all baseline RF signals and US measurement in a database, and providing an operator an identification of a drug/solution mixture and printing or affixing at least one of a barcode, a machine-readable object, an RFID tag, and a text to a liquid-filled IV bag to indicate a content of a liquid-filled IV bag (1078). Identifying a content of a liquid-filled IV bag may include: identifying a liquid base of a liquid in an IV bag; identifying one or more drugs present in a liquid base; and identifying a concentration of one or more drugs in a liquid base. In a non-limiting example, an unknown liquid may be identified as lidocaine with a concentration of 2 mg/ml. In another non-limiting example, an unknown liquid may be identified as a saline solution with a concentration of 0.9%/1000 ml. In an alternative embodiment to (1078) of method 1000, a drug/solution mixture may not be identified by comparing received RF signal and US measurement against all baseline RF signals and US measurements in a database, and RF signals and US measurements of unidentified drug/solution mixture may be stored in a database for later identification. In an alternative embodiment to (1078) of method 1000, an identification of a drug/solution mixture may include outputting an identification of a drug/solution mixture to a display such as a computer monitor. Identification of a drug/solution mixture may include a name of a drug/solution mixture, a chemical representation of a drug/solution mixture, a concentration of a drug/solution mixture, and the like. Method 1000 may include interrogation and identification of a drug/solution mixture in other containers such as syringes, vials, bottles, and the like.

Any of the aforementioned systems and systems executing interrogation and identification methods described herein may further be networked to one another. A network may be a telecommunications network that may allow systems to communicate with each other and exchange data. Network links may be either wired or wireless, and nodes connecting systems to network links may be either wired or wireless. Networked systems may include software and hardware essential for networking-including, but not limited to one or more: modems, hubs, bridges, switches, host computers, routers, workstations, servers, and the like. In one embodiment, each system and system executing methods described herein has its own dedicated database. In another embodiment, a system and system executing methods described herein may share a remote database with one or more similar systems. Networked systems may interact with a hospital and pharmacy networks to allow for database updates, remote use of systems, and remote troubleshooting. For example, an unidentified liquid may be sent from a networked system to a remote, shared database and/or another system and be identified from a liquid signature already stored in the remote, shared database and/or other system. In another embodiment, a remote bar scanner scans a barcoded IV bag and sends the scanned barcode via a networked system to a database for identification of contents in a liquid-filled IV bag based on the scanned barcode.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

As used in the specification and the claims, the singular forms "a," "an," and "the" include the plural. To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11

What is claimed is:

1. A method comprising:
applying a radio-frequency (RF) signal to a liquid;
monitoring for an RF response signal comprising at least one of a reflected RF signal and a coupled RF signal in response to the applying of the RF signal to the liquid;
analyzing the RF response signal to determine an RF signal measurement in one of a frequency domain and a time domain;
comparing the RF signal measurement with one or more baseline RF signal measurements;
applying an ultrasonic signal to the liquid;
monitoring for an ultrasonic response signal in response to the applying of the ultrasonic signal to the liquid;
analyzing the ultrasonic response signal to determine an ultrasonic measurement;
comparing the ultrasonic measurement with one or more baseline ultrasonic measurements; and
determining an identity of the liquid or predicting an identity of the liquid based on the comparison of the RF signal measurement with the one or more baseline RF signal measurements and further based on the comparison of the ultrasonic measurement with the one or more baseline ultrasonic measurements.

2. The method of claim 1, further comprising:
calculating a temperature compensation factor based on a temperature of the liquid sample;
applying the temperature compensation factor to one of: the one or more baseline RF signal measurements and the one or more baseline ultrasonic measurements prior to one of the comparing of the RF signal measurement with the one or more baseline RF signal measurements and the comparing of the ultrasonic measurement with the one or more baseline ultrasonic measurements.

3. The method of claim 2,
wherein the applying the ultrasonic signal to the liquid comprises producing one or more pulse echoes;
wherein the monitoring for the ultrasonic response signal comprises:
receiving the one or more pulse echoes;
generating an electrical signal representative of the one or more pulse echoes; and
analyzing the electrical signal to determine the ultrasonic measurement, wherein the ultrasonic measurement comprises one of an ultrasonic velocity of the liquid and an attenuation of the one or more pulse echoes caused by the liquid; and
wherein the comparing the ultrasonic measurement with the one or more baseline ultrasonic measurements comprises one of comparing the ultrasonic velocity of the liquid with one or more baseline ultrasonic velocities and comparing the attenuation of the one or more pulse echoes caused by the liquid with one or more baseline attenuations.

4. The method of claim 3,
wherein the generating the electrical signal representative of the one or more pulse echoes comprises:
generating an analog signal representative of the one or more pulse echoes; and
digitizing the analog signal to generate a representative digital signal; and
wherein the analyzing the electrical signal to determine the ultrasonic measurement comprises analyzing the representative digital signal to determine the ultrasonic velocity of the liquid and the attenuation of the one or more pulse echoes caused by the liquid.

5. The method of claim 4, further comprising:
applying a pressure to a container comprising the liquid;
measuring the pressure applied to the container; and
adjusting an amount of the pressure applied to the container until the pressure applied to the container is equal to a baseline pressure.

6. The method of claim 5, further comprising determining a path length distance of a container comprising the liquid, wherein the analyzing of the ultrasonic response signal is based on the determined path length distance.

7. The method of claim 1, wherein the RF signal measurement comprises one of one or more S-parameters, a center frequency, a level of impedance match, a current, a voltage drop, the RF signal measurement in a time domain, the RF signal measurement in a frequency domain, a Fast Fourier Transform (FFT) ratio of two or more RF signal measurements, an FFT difference of two or more RF signal measurements, the RF signal measurement to which a time domain algorithm has been applied and two or more RF signal measurements to which a Partial Least Squares (PLS) regression has been applied.

8. The method of claim 7, wherein the RF signal measurement comprises one of: a real value, an imaginary value, a complex value, a magnitude, or a phase.

9. The method of claim 8, wherein the monitoring for the ultrasonic response signal comprises monitoring for the ultrasonic response signal according to a time delay, wherein the time delay defines a period of time between applying the ultrasonic signal and a reception of the ultrasonic response signal.

10. The method of claim 1, wherein the applying the ultrasonic signal to the liquid is at an ultrasonic transmitter, and the monitoring for the ultrasonic response signal in response to the applying the ultrasonic signal to the liquid is at an ultrasonic receiver.

11. The method of claim 10, further comprising coupling the ultrasonic transmitter to a side of a container comprising the liquid and the ultrasonic receiver to another side of the container.

12. The method of claim 1, further comprising:
applying a pressure to a container comprising the liquid;
measuring the pressure applied to the container; and
adjusting an amount of the pressure applied to the container until the pressure applied to the container is equal to a baseline pressure.

13. The method of claim 1, further comprising:
generating a high-voltage pulse;
generating the ultrasonic signal based on the high-voltage pulse, wherein the applying the ultrasonic signal to the liquid comprises producing one or more pulse echoes; and
wherein the monitoring for the ultrasonic response signal comprises monitoring for the ultrasonic response signal according to a time delay, wherein the time delay defines a period of time between applying the ultrasonic signal and reception of the ultrasonic response signal.

14. The method of claim 1, further comprising:
determining a path length distance of a container comprising the liquid; and
wherein the analyzing the ultrasonic response signal is based on the determined path length distance.

15. The method of claim 1, wherein the applying the RF signal to the liquid comprises applying an RF signal between 100 Megahertz (MHz) and 15 Gigahertz (GHz) to the liquid.

16. The method of claim 1, wherein the applying the RF signal to the liquid comprises applying an RF signal to the liquid according to a frequency sweep with a varying frequency between 100 Megahertz (MHz) and 15 Gigahertz (GHz).

17. The method of claim 1, wherein the applying the RF signal to the liquid comprises introducing the RF signal to the liquid by one of one or more wide band antennas, one or more narrow band antennas, a coaxial probe, a conductive pattern and a diode grid array.

18. The method of claim 1, wherein the monitoring for the RF response signal comprises monitoring for the RF response signal by one of one or more wide band antennas, one or more narrow band antennas, a coaxial probe, a conductive pattern, and a diode grid array.

19. The method of claim 1, wherein the applying the ultrasonic signal to the liquid and the monitoring for the ultrasonic response signal in response to the applying of the ultrasonic signal to the liquid is at an ultrasonic sensor.

20. The method of claim 1, wherein the monitoring for the ultrasonic response signal comprises monitoring for the ultrasonic response signal according to a time delay, wherein the time delay defines a period of time between applying the ultrasonic signal and reception of the ultrasonic response signal.

21. The method of claim 1, wherein the ultrasonic response signal is an analog signal, and wherein the analog signal is converted into a a digital signal, and wherein the digital signal is analyzed to determine the ultrasonic measurement.

22. A method for identifying a drug/solution mixture contained in an intravenous (IV) bag comprising:
receiving a liquid-filled IV bag;
determining a presence of at least one of: a barcode, a machine-readable object, a radio frequency identification (RFID) tag, and a text identifying a liquid in the liquid-filled IV bag;
scanning the at least one of: the barcode, the machine-readable object, the RFID tag, and the text, if present, to generate an input data;
comparing the input data with baseline data in a database;
generating an alert in response to the comparison indicating that the input data is not in the database;
transmitting a radio frequency (RF) signal to interrogate the liquid in the liquid-filled IV bag in response to the comparison indicating that the input data is in the database;
monitoring for an RF response signal in response to interrogating the liquid with the RF signal;

transmitting an ultrasonic signal to interrogate the liquid in the liquid-filled IV bag;

monitoring for an ultrasonic response signal in response to interrogating the liquid with the ultrasonic signal, wherein the monitoring comprises analyzing the ultrasonic response signal to determine an ultrasonic measurement;

measuring a temperature of the liquid in the liquid-filled IV bag;

applying a temperature compensation to of baseline RF signals and baseline ultrasonic measurements in the database based on the measured temperature of the liquid;

comparing the RF response signal to the baseline RF signals in the database and the ultrasonic measurement to the baseline ultrasonic measurements in the database; and identifying a drug/solution mixture of the liquid or predicting an identity of the drug/solution mixture of the liquid based on the comparison of the RF response signal to the baseline RF signals and further based on the comparison of the ultrasonic measurement to the baseline ultrasonic measurements.

23. The method of claim 22, further comprising:
providing a user device with at least one of an identification of the drug/solution mixture and a prediction of the drug/solution mixture.

24. The method of claim 23, further comprising:
printing or affixing at least one of: a barcode, a machine-readable object, an RFID tag, and a text to the liquid-filled IV bag to identify the drug/solution mixture.

25. The method of claim 24, further comprising:
providing the liquid-filled IV bag in a test fixture; and
applying a predetermined amount of pressure to the liquid-filled IV bag in the test fixture.

26. The method of claim 22, further comprising:
determining a path length distance of the liquid-filled IV bag; and
wherein the analyzing of the ultrasonic response signal is based on the determined path length distance.

* * * * *